United States Patent [19]

Iwamatsu et al.

[11] Patent Number: 5,631,257
[45] Date of Patent: May 20, 1997

[54] BENZOXAZOLE DERIVATIVES

[75] Inventors: Katsuyoshi Iwamatsu; Yasuo Sato; Masaaki Izumi; Fukio Konno; Seiji Shibahara; Shigeharu Inoye, all of Kanagawa; Koichi Shudo, Tokyo; Kazuko Amano, Kanagawa, all of Japan

[73] Assignees: Meiji Seika Kaisha, Ltd.; Koichi Shudo, both of Tokyo, Japan

[21] Appl. No.: 487,697

[22] Filed: Jun. 7, 1995

Related U.S. Application Data

[63] Continuation of Ser. No. 228,894, Apr. 18, 1994, abandoned.

[30] Foreign Application Priority Data

Apr. 16, 1993 [JP] Japan ........................... 5-090086
Mar. 14, 1994 [JP] Japan ........................... 6-042909

[51] Int. Cl.⁶ .................... A61K 31/495; A61K 31/55; C07D 401/00; C07D 419/00
[52] U.S. Cl. .................... 514/254; 514/218; 544/361; 544/368; 540/575
[58] Field of Search ................... 544/368; 514/254

[56] References Cited

U.S. PATENT DOCUMENTS 4,877,878 10/1989 Kampe et al. ........................ 544/368

FOREIGN PATENT DOCUMENTS 2083375 3/1990 Japan ........................ 544/368

OTHER PUBLICATIONS

Monge et al. CA 120:323489 (1994).
Nakao et al. CA 116:194290 (1992).
Ogawa et al. CA 114:102062 (1990).
Ray et al. CA 112:21013 (1989).
Verderame. CA 69:106666 (1968).
Tomcufcik et al. CA 67:90839 (1967).

*Primary Examiner*—Cecilia Tsang
*Attorney, Agent, or Firm*—Sughrue, Mion, Zinn, Macpeak & Seas

[57] ABSTRACT

A benzoxazole derivative of the formula (1) or (2) which has an alicyclic diamine group at the 2-position:

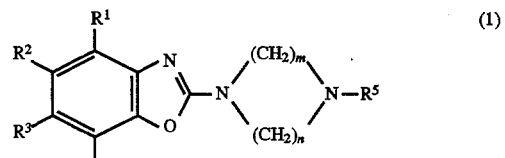

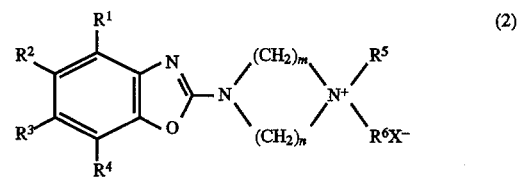

wherein $R^1$, $R^2$, $R^3$, $R^4$, $R^5$, $R^6$, $X^-$, m and n are defined herein. The compound shows excellent 5-HT$_3$ receptor antagonism and is useful as an antiemetic agent, a peristalsis controlling agent, an analgesic agent, an antianxiety agent and a schizophrenia treating agent.

9 Claims, No Drawings

BENZOXAZOLE DERIVATIVES

This is a continuation of application Ser. No. 08/228,894 filed Apr. 18, 1994 now abandoned.

FIELD OF THE INVENTION

This invention relates to benzoxazole derivatives which show serotonin 5-$HT_3$ receptor antagonism.

BACKGROUND OF THE INVENTION

In recent years, compounds having serotonin 5-$HT_3$ receptor antagonism have been studied extensively and some of them are now used in the clinical field, because of their function to repress nausea and emesis as side effects caused by the use of carcinostatic agents such as cisplatin and the like or by radiotherapy. However, as is evident in benzamide base drugs, these prior art compounds are not always satisfactory in view of their drug effects free from side effects.

SUMMARY OF THE INVENTION

An object of the invention is to provide a compound having an excellent serotonin 5-$HT_3$ receptor antagonism.

The inventors of the present invention have reported recently that a benzothiazole derivative has an excellent cardiotonic effect (JP-A-4-316565) (The term "JP-A" as used herein means an "unexamined published Japanese patent application"). Thereafter, the present inventors have continued studies on the synthesis of new derivatives and found that a benzoxazole derivative has a strong and selective 5-$HT_3$ receptor antagonism.

Since the 5-$HT_3$ receptor antagonist is possessed of not only antiemetic effect but also peristalsis enhancing effect, analgesic effect, antianxiety effect and the like, it is also useful as a peristalsis controlling agent, an analgesic, an antianxiety agent and an agent for the treatment of schizophrenia.

The present invention provides a compound represented by the formula (1)

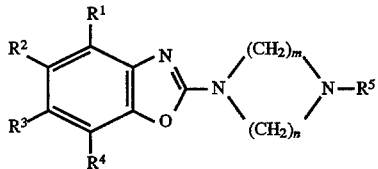

(1)

wherein $R^1$, $R^2$, $R^3$ and $R^4$ may be the same or different and each represents a hydrogen atom, a substituted or unsubstituted lower alkyl group, a substituted or unsubstituted lower alkenyl group, a halogen atom, a hydroxyl group, an amino group, a lower alkoxyl group, a carboxyl group, a carbamoyl group or a nitro group, in which any two groups of $R^1$ to $R^4$ may be linked to each other to form a three to seven-membered ring structure comprising carbon atoms alone or carbon atoms and 1 to 2 hetero atoms, which may be substituted; $R^5$ represents a substituted or unsubstituted lower alkyl group, a substituted or unsubstituted lower alkenyl group, a substituted or unsubstituted aralkyl group or an alkoxycarbonyl group; and m and n may be the same or different and each is an integer of 1 to 3, and a compound represented by the formula (2)

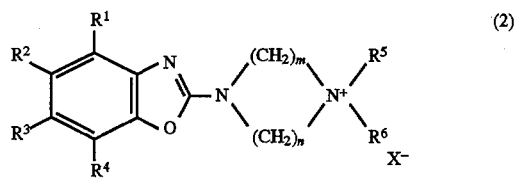

(2)

wherein $R^1$, $R^2$, $R^3$ and $R^4$ may be the same or different and each represents a hydrogen atom, a substituted or unsubstituted lower alkyl group, a substituted or unsubstituted lower alkenyl group, a halogen atom, a hydroxyl group, an amino group, a lower alkoxyl group, a carboxyl group, a carbamoyl group or a nitro group, in which any two groups of $R^1$ to $R^4$ may be linked to each other to form a three to seven-membered ring structure comprising carbon atoms alone or carbon atoms and 1 to 2 hetero atoms, which may be substituted; $R^5$ and $R^6$ may be the same or different and each represents a substituted or unsubstituted lower alkyl group, a substituted or unsubstituted lower alkenyl group or a substituted or unsubstituted aralkyl group or an alkoxycarbonyl group, in which $R^5$ and $R^6$ may be linked to each other to form a three to seven-membered ring structure comprising carbon atoms and 1 to 2 nitrogen atoms, which may be substituted; $X^-$ represents a pharmaceutically acceptable anion; and m and n may be the same or different and each is an integer of 1 to 3.

Further, the present invention provides a 5-$HT_3$ receptor antagonist which comprises the compound represented by the above formula (1) or (2) as an active ingredient and a pharmaceutically acceptable carrier.

DETAILED DESCRIPTION OF THE INVENTION

According to the present invention, the alkyl moiety of lower alkyl and lower alkoxyl groups may preferably be a straight or branched-chain $C_{1-6}$ alkyl group, and the lower alkenyl group may preferably be a straight or branched-chain $C_{2-6}$ alkenyl group. The aralkyl group contains 7 to 10 carbon atoms. Illustrative examples of substituent groups include a halogen atom and hydroxyl, cyano, acyl, alkoxy, carboxyl, alkoxycarbonyl, carbamoyl, amino, nitro and the like groups. Examples of halogen atoms include fluorine, chlorine, bromine, and iodine. The alkyl moiety of the acyl, alkoxy and alkoxycarbonyl groups contain 1 to 6 carbon atoms. The three to seven-membered ring composed of any two of $R^1$ to $R^4$ may include nitrogen, oxygen or sulfur as a hetero atom. Examples of the ring include benzene ring, cyclohexane ring, pyridine ring, piperidine ring, pyrrolidine ring and the like. Examples of the three to seven-membered ring composed of $R^5$ and $R^6$ include aziridine ring, pyrrolidine ring, piperidine ring, homopiperidine ring and the like. The pharmaceutically acceptable anion includes halogen ion, sulfate anion, phosphate anion or organic acid anion such as acetate or formate anion. The methylene group of the moiety of

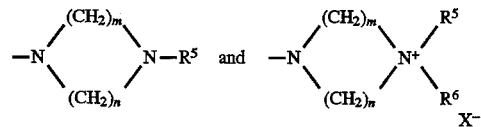

may be substituted with $C_{1-6}$ alkyl, $C_{2-6}$ alkenyl, $C_{2-6}$ alkynyl halogen, nitro, amino, $C_{1-6}$ alkoxyl, carboxyl, hydroxyl, carbamoyl and the like groups.

The compound of formula (1) of the present invention can be produced by various methods, but preferably by the following two typical methods.

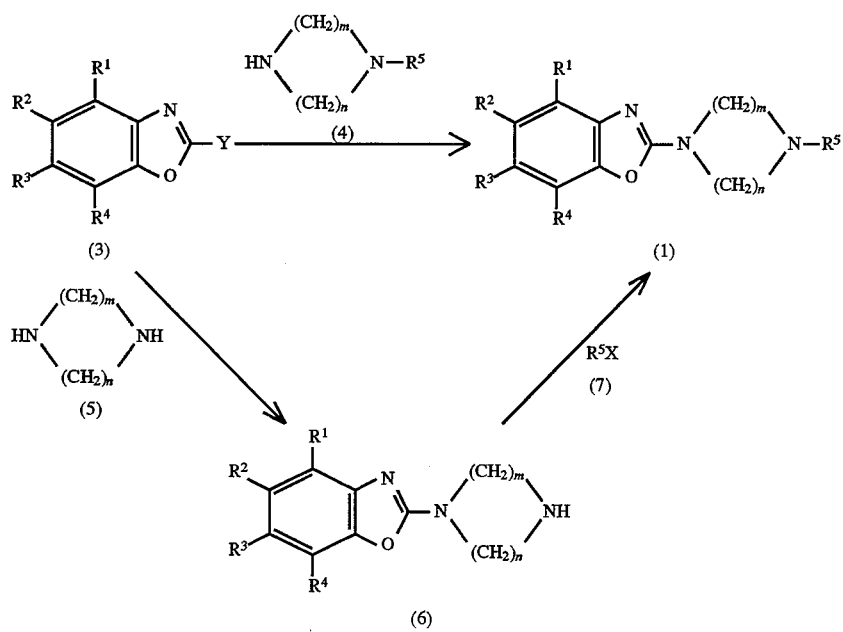

A compound of interest represented by the formula (1), in which $R^1, R^2, R^3, R^4, R^5$, m and n are defined above, can be obtained by allowing a compound represented by the formula (3), in which $R^1, R^2, R^3$ and $R^4$ are defined above and Y represents a halogen atom, to react with an N-substituted alicyclic diamine represented by the formula (4), in which $R^5$, m and n are defined above.

Alternatively, a compound of interest represented by the formula (1), in which $R^1, R^2, R^3, R^4, R^5$, m and n are defined above, can be obtained by allowing a compound represented by the formula (3), in which $R^1, R^2, R^3$ and $R^4$ are defined above and Y represents a halogen atom, to react with an alicyclic diamine represented by the formula (5), in which m and n are defined above, thereby obtaining a compound represented by the formula (6), in which $R^1, R^2, R^3$ and $R^4$ are defined above, and subsequently allowing the compound (6) to react with a compound represented by the formula (7), in which $R^5$ is defined above and X represents a halogen atom.

The compound represented by the formula (2) can be produced by the following method.

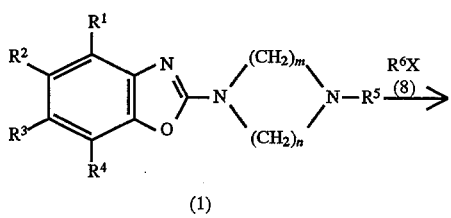

A compound of interest represented by the formula (2) can be obtained by allowing a compound represented by the formula (1), in which $R^1, R^2, R^3, R^4, R^5$, m and n are defined above, to react with a compound represented by the formula (8), in which $R^6$ is defined above and X represents a halogen atom.

Reaction of the compound (3) with the compound (4) or (5) progresses quickly when the reaction is carried out at a temperature of from 0° to 150° C. without using solvents or in a solvent such as dimethylformamide (DMF) or the like. The reaction can be carried out in the presence of a base if necessary.

The compound (1) can be obtained easily by carrying out reaction of the compound (6) with the compound (7) at a temperature of from 0° to 80° C. for 1 hour to 5 days in a solvent such as DMF or the like. The compound (2) can be obtained from the compounds (1) and (8) in the same manner.

The thus obtained compound can be isolated and purified by conventional methods including recrystallization or chromatography.

The compound of the present invention may be formulated into a pharmaceutical composition together with known pharmaceutically acceptable carriers. These compositions may be orally or parenterally administered. Examples of oral dosage forms include tablets, capsules, granules, powders and the like. In the case of parenteral administration, the compound may be formulated into a solution, a suspension and the like and administered intravenously, subcutaneously or intramuscularly.

The composition of the present invention may be given to an adult in a dose of 0.01 to 5 mg/kg/day in terms of the active ingredient by injection, intravenous drip or oral administration.

The following examples are provided to further illustrate the present invention. It is to be understood, however, that the examples are for purpose of illustration only and are not to be construed to limit the scope of the present invention, and various alterations and modifications can be made within the scope of the present invention. In the following examples, NMR data are shown as δ values measured by 300 MHz NMR using TMS as the standard.

EXAMPLE 1

2-(4-Methyl-1-piperazinyl)benzoxazole

To 3.08 g of 2-chlorobenzoxazole was added 200 ml of N-methylpiperazine under cooling with ice, followed by 2 hours of reaction at the same temperature. The reaction mixture was concentrated under a reduced pressure, and the resulting residue was dissolved in 200 ml of ethyl acetate, washed with water, dehydrated with $MgSO_4$ and then concentrated to dryness under a reduced pressure. The resulting residue was purified by a silica gel column chromatography (chloroform:methanol=20:1) to obtain 2.77 g of the title compound.

NMR ($CDCl_3$) δ: 7.37 (1H, d), 7.26 (1H, d), 7.18 (1H, t), 7.02 (1H, t), 3.73 (4H, t), 2.54 (4H, t), 2.37 (3H, s)

EXAMPLE 2

1,1-Dimethyl-4-(benzoxazol-2-yl)piperazinium iodide

A 435 mg portion of 2-(4-methyl-1-piperazinyl) benzoxazole was dissolved in 6 ml of DMF. Under cooling with ice, 0.19 ml of methyl iodide was added to the thus prepared solution, and the reaction was carried out for 1 hour at the same temperature and then for 1 hour at room temperature. The reaction solution was concentrated under a reduced pressure, and 4 ml of acetone was added to the resulting residue. The precipitate thus formed was collected by filtration, washed with acetone and then dried to obtain 670 mg of the title compound.

NMR (DMSO-$d_6$) δ: 7.48 (1H, d), 7.37 (1H, d), 7.22 (1H, t), 7.10 (1H, t), 3.99 (4H, t), 3.58 (4H, t), 3.23 (6H, s)

EXAMPLE 3

1-Allyl-1-methyl-4-(benzoxazol-2-yl)piperazinium iodide

A 1.09 g portion of 2-(4-methyl-1-piperazinyl)-benzoxazole and 0.69 ml of allyl iodide were treated in the same manner as in Example 2 to obtain 1.88 g of the title compound.

NMR (DMSO-$d_6$) δ: 7.48 (1H, d), 7.38 (1H, d), 7.21 (1H, t), 7.10 (1H, t), 6.10 (1H, m), 5.71 (2H, dd), 4.18 (2H, d), 4.15–3.9 (4H, m), 3.56 (4H, t), 3.15 (3H, s)

EXAMPLE 4

1-Allyl-1-methyl-4-(benzoxazol-2-yl)piperazinium chloride

Using 435 mg of 2-(4-methyl-1-piperazinyl)benzoxazole and 0.24 ml of allyl chloride, the same treatment of Example 2 was conducted to obtain 504 mg of the title compound.

NMR ($CD_3OD$) δ: 7.39 (1H, d), 7.37 (1H, d), 7.23 (1H, t), 7.14 (1H, t), 6.20–6.10 (1H, m), 5.82–5.78 (2H, m), 4.20–4.17 (4H, m), 4.04–3.96 (2H, m), 3.70–3.60 (4H, m), 3.24 (3H, s)

EXAMPLE 5

1-(2-Hydroxyethyl)-1-methyl-4-(benzoxazol-2-yl) piperazinium iodide

A 435 mg portion of 2-(4-methyl-1-piperazinyl)-benzoxazole was dissolved in 3 ml of DMF. Under cooling with ice, 0.24 ml of 2-iodoethyl alcohol was added to the thus prepared solution, and the reaction was carried out for 1 hour at the same temperature and then for 17 hours at room temperature, followed by further addition of 0.48 ml 2-iodoethyl alcohol and subsequent 21 hours of reaction at 50° C. The reaction mixture was concentrated under a reduced pressure, and 5 ml of acetone was added to the resulting residue. The precipitate thus formed was collected by filtration, washed with acetone and then dried to obtain 583 mg of the title compound.

NMR ($CD_3OD$) δ: 7.40 (1H, d), 7.35 (1H, d), 7.21 (1H, t), 7.12 (1H, t), 4.15–4.05 (6H, m), 3.88–3.80 (2H, m), 3.80–3.70 (4H, m), 3.42 (3H, s)

EXAMPLE 6

1-Benzyl-1-methyl-4-(benzoxazol-2-yl)piperazinium bromide

A 300 mg portion of 2-(4-methyl-1-piperazinyl)-benzoxazole was dissolved in 5 ml of THF. Under cooling with ice, 354 mg of benzyl bromide was added to the thus prepared solution, and the reaction was carried out for 1 hour at the same temperature and then for 22 hours at room temperature. The thus formed precipitate was collected by filtration and washed with acetone. The filtrate was concentrated under a reduced pressure, and the resulting residue was dissolved in 50 ml of water, washed with ethyl acetate and then lyophilized to obtain 496 mg of the title compound.

NMR ($CD_3OD$) δ: 7.90 (1H, s), 7.63–7.56 (4H, m), 7.40 (1H, d), 7.36 (1H, d), 7.23 (1H, t), 7.13 (1H, t), 4.74 (2H, s), 4.29 (2H, brd), 3.98–3.92 (2H, m), 3.77–3.72 (2H, m), 3.60 (2H, brd), 3.17 (3H, s)

EXAMPLE 7

1-Cyanomethyl-1-methyl-4-(benzoxazol-2-yl) piperazinium bromide

A 150 mg portion of 2-(4-methyl-1-piperazinyl)-benzoxazole was dissolved in 3 ml of DMF. Under cooling with ice, 0.052 ml of bromoacetonitrile was added to the thus prepared solution, and the reaction was carried out for 1 hour at the same temperature and then for 24 hours at room temperature. The reaction solution was concentrated under a reduced pressure, and 5 ml of acetone was added to the resulting residue. The precipitate thus formed was collected by filtration, washed with acetone and then dried to obtain 228 mg of the title compound.

NMR ($CD_3OD$) δ: 7.40 (1H, d), 7.37 (1H, d), 7.23 (1H, t), 7.14 (1H, t), 5.06 (2H, s), 4.27–4.21 (2H, m), 4.10–4.03 (2H, m), 3.93–3.83 (4H, m), 3.52 (3H, s)

EXAMPLE 8

1-Ethoxycarbonylmethyl-1-methyl-4-(benzoxazol-2-yl)piperazinium bromide

A 110 mg portion of 2-(4-methyl-1-piperazinyl)-benzoxazole was dissolved in 3 ml of DMF. Under cooling with ice, 101 mg of bromoethyl acetate was added to the thus prepared solution, and the reaction was carried out for 1 hour at the same temperature and then for 84 hours at room temperature. The reaction solution was concentrated under a reduced pressure, and 5 ml of acetone was added to the resulting residue. The precipitate thus formed was collected by filtration, washed with acetone and then dried to obtain 167 mg of the title compound.

NMR (CD$_3$OD) δ: 7.41 (1H, d), 7.38 (1H, d), 7.25 (1H, t), 7.15 (1H, t), 4.60 (2H, s), 4.36 (2H, q), 4.20–4.05 (4H, m), 3.99–3.88 (4H, m), 3.52 (3H, s), 1.36 (3H, t)

EXAMPLE 9

1-Acetonyl-1-methyl-4-(benzoxazol-2-yl) piperazinium bromide

A 100 mg portion of 2-(4-methyl-1-piperazinyl)-benzoxazole was dissolved in 3 ml of DMF. Under cooling with ice, 95 mg of bromoacetone was added to the thus prepared solution, and the reaction was carried out for 1 hour at the same temperature and then for 60 hours at room temperature. The reaction solution was concentrated under a reduced pressure, and 5 ml of acetone was added to the resulting residue. The precipitate thus formed was collected by filtration, washed with acetone and then dried to obtain 119 mg of the title compound.

NMR (CD$_3$OD) δ: 7.39 (1H, d), 7.36 (1H, d), 7.22 (1H, t), 7.13 (1H, t), 4.81 (2H, s), 4.15–4.05 (4H, m), 3.97–3.80 (4H, m), 3.47 (3H, s), 2.27 (3H, s)

EXAMPLE 10

8-(Benzoxazol-2-yl)-8-aza-5-azoniaspiro[4,5]decane iodide

A 3.07 g portion of 2-chlorobenzoxazole was dissolved in 10 ml of dichloromethane. Under cooling with ice, to this was added dropwise 3.45 g of anhydrous piperazine which has been dissolved in 30 ml of dichloromethane, followed by 1 hour of reaction. The reaction solution was concentrated under a reduced pressure, and the resulting residue was purified by a silica gel column chromatography (dichloromethane:methanol=20:1), followed by concentration of the eluate under a reduced pressure. Thereafter, the resulting residue was dissolved in 30 ml of water, neutralized with 1N hydrochloric acid, extracted with dichloromethane, washed with water, dehydrated with Na$_2$SO$_4$ and then concentrated under a reduced pressure to obtain 1.77 g of 2-(1-piperazinyl)benzoxazole.

A 245 mg portion of potassium carbonate was added to 300 mg of 2-(1-piperazinyl)benzoxazole which had been dissolved in 5 ml of DMF, and the reaction was carried out for 30 minutes. Under cooling with ice, 0.23 ml of 1,4-diiodobutane was added to the resulting solution, and the reaction was carried out for 1 hour at the same temperature and then for 2 hours at room temperature. The reaction solution was concentrated under a reduced pressure, and the resulting residue was dissolved in 300 ml of dichloromethane and extracted three times with 100 ml of water. Thereafter, the aqueous layers were combined and lyophilized. By purifying the residue by Diaion HP-20 (Mitsubishi Chemicals), 175 mg of the title compound was obtained.

NMR (CD$_3$OD) δ: 7.39 (1H, d), 7.36 (1H, d), 7.23 (1H, t), 7.12 (1H, t), 4.06 (4H, brs), 3.75 (4H, t), 3.70 (4H, t), 2.28 (4H, brs)

EXAMPLE 11

2-[4-(2-Hydoxyethyl)-1-piperazinyl]benzoxazole

A 300 mg portion of 2-chlorobenzoxazole was dissolved in 2 ml of DMF. Under cooling with ice, 279 mg of 1-(2-hydroxyethyl)piperazine was added to the thus prepared solution, and the reaction was carried out for 1 hour at the same temperature and then for 24 hours at room temperature. The reaction solution was concentrated under a reduced pressure, and the resulting residue was dissolved in 100 ml of ethyl acetate and washed with sodium hydrogencarbonate aqueous solution (pH 8) and then with water. The resulting organic layer was dehydrated with sodium sulfate and concentrated under a reduced pressure to obtain 140 mg of the title compound.

NMR (CD$_3$OD) δ: 7.31 (1H, d), 7.28 (1H, d), 7.17 (1H, t), 7.05 (1H, t), 3.72–3.68 (6H, m), 2.65 (4H, t), 2.58 (2H, t)

EXAMPLE 12

1,1-[Di(2-hydroxyethyl)]-4-(benzoxazol-2-yl) piperazinium iodide

A 100 mg portion of 2-[4-(2-hydroxyethyl)-1-piperazinyl] benzocazole was dissolved in 5 ml of DMF. A 105 mg portion of 2-iodoethyl alcohol was added to the thus prepared solution, and the reaction was carried out for 48 hours at 60° C. and then for 5 hours at 90° C. The reaction mixture was concentrated under a reduced pressure, and 5 ml of acetone was added to the resulting residue. The precipitate thus formed was collected by filtration, washed with acetone and then dried to obtain 80 mg of the title compound.

NMR (CD$_3$OD) δ: 7.39 (1H, d), 7.35 (1H, d), 7.23 (1H, t), 7.13 (1H, t), 4.11–4.08 (8H, m), 3.89–3.85 (8H, m)

EXAMPLE 13

2-(4-Methyl-1-homopiperazinyl)benzoxazole

A 1.54 g portion of 2-chlorobenzoxazole was dissolved in 5 ml of dichloromethane. Under cooling with ice, to this was added dropwise 2.28 g of N-methylhomopiperazine which had been dissolved in 10 ml of dichloromethane, followed by 1 hour of reaction. The reaction solution was concentrated under a reduced pressure, and the resulting residue was dissolved in 500 ml of dichloromethane, washed with water, dehydrated with sodium sulfate and then concentrated under a reduced pressure. Thereafter, the resulting residue was purified by a silica gel column chromatography (chloroform:methanol=10:1) to obtain 1.87 g of the title compound.

NMR (CD$_3$OD) δ: 7.30 (1H, d), 7.26 (1H, d), 7.16 (1H, t), 7.02 (1H, t), 3.83–3.76 (4H, m), 2.81–2.78 (2H, m), 2.67–2.65 (2H, m), 2.39 (3H, s), 2.07–2.00 (2H, m)

EXAMPLE 14

1,1-Dimethyl-4-(benzoxazol-2-yl)homopiperazinium iodide

A 200 mg portion of 2-(4-methyl-1-homopiperazinyl)-benzoxazole was dissolved in 5 ml of tetrahydrofuran (THF). Under cooling with ice, 0.064 ml of methyl iodide was added to the thus prepared solution, and the reaction was carried out for 1 hour at the same temperature and then for 2 hours at room temperature. The reaction solution was concentrated under a reduced pressure, and 5 ml of acetone was added to the resulting residue. The precipitate thus formed was collected by filtration, washed with acetone and then dried to obtain 320 mg of the title compound.

NMR (CD$_3$OD) δ: 7.36 (1H, d), 7.31 (1H, d), 7.20 (1H, t), 7.08 (1H, t), 4.13–4.12 (2H, m), 3.92–3.85 (2H, m), 3.78–3.75 (2H, m), 3.70–3.67 (2H, m), 3.31 (3H, s), 3.30 (3H, s), 2.38 (2H, brs)

EXAMPLE 15

1-Allyl-1-methyl-4-(benzoxazol-2-yl) homopiperazinium iodide

A 540 mg portion of 2-(4-methyl-1-homopiperazinyl)-benzoxazole was dissolved in 5 ml of dichloromethane. Under cooling with ice, 0.32 ml of allyl iodide was added to the thus prepared solution, and the reaction was carried out for 1 hour at the same temperature and then for 1 hour at room temperature. The reaction solution was concentrated under a reduced pressure, and 5 ml of acetone was added to the resulting residue. The precipitate thus formed was collected by filtration, washed with acetone and then dried to obtain 821 mg of the title compound.

NMR (CD$_3$OD) δ: 7.36 (1H, d), 7.31 (1H, d), 7.20 (1H, t), 7.08 (1H, t), 6.19–6.09 (1H, m), 5.80–5.75 (2H, m), 4.22–4.12 (4H, m), 3.91 (2H, t), 3.78–3.74 (2H, m), 3.70–3.67 (2H, m), 3.19 (3H, s), 2.41 (2H, brs)

EXAMPLE 16

1-(2-Hydroxyethyl)-1-methyl-4-(benzoxazol-2-yl) homo-piperazinium iodide

A 100 mg portion of 2-(4-methyl-1-homopiperazinyl)-benzoxazole was dissolved in 3 ml of THF. Under cooling with ice, 89 mg of 2-iodoethyl alcohol was added to the thus prepared solution, and the reaction was carried out for 1 hour at the same temperature and then for 29 hours at room temperature. The reaction solution was concentrated under a reduced pressure, and 3 ml of acetone was added to the resulting residue. The precipitate thus formed was collected by filtration, washed with acetone and then dried to obtain 143 mg of the title compound.

NMR (CD$_3$OD) δ: 7.36 (1H, d), 7.31 (1H, d), 7.20 (1H, t), 7.08 (1H, t), 4.16–3.64 (12H, m), 3.31 (3H, s), 2.39 (2H, brs)

EXAMPLE 17

2-(1-Homopiperazinyl)benzoxazole

A 978 mg portion of homopiperazine was dissolved in 3 ml of DMF. Under cooling with ice, 500 mg of 2-chlorobenzoxazole was added to the thus prepared solution, and the reaction was carried out for 1 hour at the same temperature and then for 24 hours at room temperature. The reaction solution was concentrated under a reduced pressure, and the resulting residue was dissolved in 200 ml of ethyl acetate, washed with sodium hydrogencarbonate aqueous solution (pH 8) and water in that order, dehydrated with sodium sulfate and then concentrated under a reduced pressure. Thereafter, the resulting residue was purified by a silica gel column chromatography (chloroform:methanol=10:1) to obtain 540 mg of the title compound.

NMR (CD$_3$OD) δ: 7.30 (1H, d), 7.26 (1H, d), 7.16 (1H, t), 7.02 (1H, t), 3.82–3.76 (4H, m), 3.06–3.03 (2H, m), 2.90–2.87 (2H, m), 1.99–1.93 (2H, m)

EXAMPLE 18

8-Benzoxazol-2-yl)-8-aza-5-azoniaspiro[4,6] undecane iodide

A 348 mg portion of 2-(1-homopiperazinyl)benzoxazole was dissolved in 5 ml of DMF, and 221 mg of potassium carbonate was added to the solution, followed by 10 minutes of reaction. Under cooling with ice, 0.253 ml of 1,4-diiodobutane was added to the resulting solution, and the reaction was carried out for 1 hour at the same temperature and then for 24 hours at room temperature, followed by the addition of 221 mg potassium carbonate and subsequent 15 hours of reaction at 70° C. The reaction solution was concentrated under a reduced pressure, and the resulting residue was dissolved in 100 ml of dichloromethane and extracted twice with 100 ml of water. The resulting organic layers were combined and lyophilized, and the thus dried residue was purified by Diaion HP-20 (Mitsubishi Chemicals) to obtain 330 mg of the title compound.

NMR (CD$_3$OD) δ: 7.36 (1H, d), 7.31 (1H, d), 7.20 (1H, t), 7.08 (1H, t), 4.13 (2H, brs), 3.90 (2H, t), 3.76–3.60 (8H, m), 2.39 (2H, brs), 2.25 (4H, brs)

EXAMPLE 19

2-[4-(2-Hydroxyethyl)-1-homopiperazinyl] benzoxazole

A 2.329 g portion of homopiperazine dissolved in 10 ml of THF was mixed with 830 mg of iodoethyl alcohol to carry out 24 hours of reaction at room temperature. The reaction mixture was concentrated under a reduced pressure, and the resulting residue was purified by Sephadex LH-20 (Pharmacia) (chloroform:methanol=1:1) and Diaion HP-20 (Mitsubishi Chemicals) to obtain 305 mg of 1-(2-hydroxyethyl)homo-piperazine. Next, Under cooling with ice, 150 mg of 1-(2-hydroxyethyl)homopiperazine and 159 mg of 2-chlorobenzoxazole were added to 3 ml of DMF, and the reaction was carried out for 17 hours at the same temperature and then for 24 hours at room temperature. The reaction mixture was concentrated under a reduced pressure, and the resulting residue was dissolved in 100 ml of ethyl acetate, washed with sodium hydrogencarbonate aqueous solution (pH 8) and water in that order, dehydrated with sodium sulfate and then concentrated under a reduced pressure. Thereafter, the resulting residue was purified by a silica gel column chromatography (chloroform:methanol=30:1) to obtain 72 mg of the title compound.

NMR (CD$_3$OD) δ: 7.30 (1H, d), 7.27 (1H, d), 7.15 (1H, t), 7.02 (1H, t), 3.81–3.75 (4H, m), 3.65 (2H, t), 2.94–2.91 (2H, m), 2.78–2.67 (8H, m), 2.02–1.98 (2H, m)

EXAMPLE 20

2-(4-Methyl-1-piperazinyl)-6-methoxybenzoxazole

A 50 mg portion of 2-hydroxy-4-methoxyaniline hydrochloride dissolved in 15 ml of ethanol was mixed with 16 mg of potassium hydroxide. After 10 minutes of reaction, to this was added 50 ml of carbon disulfide to carry out 24 hours of heating under reflux. The reaction mixture was concentrated under a reduced pressure, and the resulting residue was dissolved in 100 ml of dichloromethane, washed with water, dehydrated with magnesium sulfate and then concentrated under a reduced pressure. The resulting residue was purified by a silica gel column chromatography (dichloromethane:methanol=30:1) to obtain 46 mg of 6-methoxy-2-mercaptobenzoxazole.

A 100 mg portion of 6-methoxy-2-mercaptobenzoxazole and 172 mg of phosphorus pentachloride were dissolved in 35 ml of chlorobenzene to carry out 8 hours of heating under reflux. The reaction solution was poured into 300 ml of ice water and extracted three times with 100 ml of dichloromethane. The resulting organic layers were combined, dehydrated with sodium sulfate, concentrated under a reduced pressure and then purified by a silica gel column chromatography (n-hexane:chloroform=1:1), to obtain 79 mg of 2-chloro-6-methoxybenzoxazole.

A 60 mg portion of 2-chloro-6-methoxybenzoxazole was dissolved in 20 ml of dichloromethane, and the reaction was carried out for 1 hour under cooling with ice and then for 72 hours at room temperature. To this was added 20 ml of THF to carry out 24 hours of heating under reflux. The reaction mixture was concentrated under a reduced pressure, and the resulting residue was dissolved in 100 ml of dichloromethane, washed with water, dehydrated with sodium sulfate and then concentrated under a reduced pressure. The resulting residue was purified by a silica gel column chromatography (n-hexane:chloroform=1:1 and chloroform:methanol=10:1) to obtain 51 mg of the title compound.

NMR (CD$_3$OD) δ: 7.17 (1H, d), 6.98 (1H, d), 6.80, 6.78 (1H, dd), 3.79 (3H, s), 3.65 (4H, t), 2.56 (4H, t), 2.35 (3H, s)

EXAMPLE 21

1-Allyl-1-methyl-4-(6-methoxybenzoxazol-2-yl) piperazinium iodide

A 50 mg portion of 2-(4-methyl-1-piperazinyl)-6-methoxybenzoxazole was dissolved in 5 ml of THF. Under cooling with ice, 0.03 ml of allyl iodide was added to the thus prepared solution, and the reaction was carried out for 1 hour at the same temperature followed by reflux for 16 hours under heating. The reaction mixture was concentrated under a reduced pressure, and the resulting residue was dissolved in 100 ml of ethyl acetate, extracted twice with 100 ml of water and then lyophilized to obtain 73 mg of the title compound.

NMR (CD$_3$OD) δ: 7.24 (1H, d), 7.05 (1H, d), 6.85, 6.83 (1H, dd), 6.18–6.10 (1H, m), 5.82–5.78 (2H, m), 4.19 (2H, d), 4.15–4.11 (2H, m), 4.00–3.90 (2H, m), 3.81 (3H, s), 3.70–3.61 (4H, m), 3.24 (3H, s)

EXAMPLE 22

1-Allyl-1-1-methyl-4-(6-hydroxybenzoxazol-2-yl) piperazinium iodide

In an atmosphere of argon gas, 150 mg of 2-chloro-6-methoxybenzoxazole dissolved in 30 ml of dichloromethane was mixed with 8.7 ml of 1.0 M BBr$_3$ dichloromethane solution and refluxed under heating for 4 hours. The reaction mixture was poured into ice water and extracted three times with 30 ml of dichloromethane. Thereafter, the resulting dichloromethane layers were combined, dehydrated with sodium sulfate and then concentrated under a reduced pressure.

Next, the resulting residue was dissolved in 3 ml of THF and, under cooling with ice, mixed with 81 mg of N-methylpiperazine to carry out 30 minutes of reaction at the same temperature. After 2 hours of heating under reflux, the resulting reaction mixture was mixed with 100 ml of chloroform and washed with water, and the water layer was neutralized and extracted with 50 ml of chloroform. The resulting chloroform layers were combined, dehydrated with sodium sulfate and then concentrated under a reduced pressure.

Next, the resulting residue was dissolved in 3 ml of THF and, under cooling with ice, mixed with 0.055 ml of allyl iodide to carry out the reaction for 1 hour at the same temperature and then for 19 hours at room temperature. To this was added 0.11 ml of allyl iodide to carry out 30 minutes of reflux under heating. The reaction mixture was concentrated under a reduced pressure, and the resulting residue was dissolved in 50 ml of water and washed with ethyl acetate. Thereafter, the resulting water layer was lyophilized and purified by Sephadex LH-20 (Pharmacia) (chloroform:methanol=1:1) to obtain 72 mg of the title compound.

NMR (CD$_3$OD) δ: 7.16 (1H, d), 6.85 (1H, d), 6.72, 6.70 (1H, dd), 6.19–6.11 (1H, m), 5.83–5.78 (2H, m), 4.19 (2H, d), 4.16–4.09 (2H, m), 4.00–3.90 (2H, m), 3.75–3.57 (4H, m), 3.23 (3H, s)

EXAMPLE 23

2-(4-Methyl-1-piperazinyl)-6-nitrobenzoxazole

A 500 mg portion of 2-amino-5-nitrophenol dissolved in 35 ml of ethanol was mixed with 180 mg of potassium hydroxide. After 10 minutes of reaction, the resulting solution was mixed with 35 ml of carbon disulfide and refluxed under heating for 48 hours. The reaction mixture was concentrated under a reduced pressure, and the resulting residue was dissolved in 300 ml of ethyl acetate and washed with an aqueous acidic solution of hydrochloric acid (pH 4) and water in that order. The resulting ethyl acetate layers were combined, dehydrated with sodium sulfate and then concentrated under a reduced pressure. Thereafter, the resulting residue was purified by a silica gel column chromatography (chloroform) to obtain 629 mg of 2-mercapto-6-nitrobenzoxazole.

A 200 mg portion of 2-mercapto-6-nitrobenzoxazole dissolved in 40 ml of anhydrous benzene was mixed with 680 mg of phosphorus pentachloride, and the mixture was refluxed under heating for 48 hours. Under cooling with ice, 2.04 g of N-methylpiperazine dissolved in 5 ml of anhydrous benzene was added to the resulting solution, and the reaction was carried out for 2 hours at the same temperature. After adding the same amount of N-methylpiperazine, the reaction was continued for additional 72 hours at room temperature. Precipitated materials in the reaction solution were removed by filtration, and the resulting filtrate was concentrated under a reduced pressure. The thus obtained residue was dissolved in 300 ml of ethyl acetate, washed three times with water, dehydrated with sodium sulfate and then concentrated under a reduced pressure. The resulting residue was purified by a silica gel column chromatography (chloroform:methanol=15:1) to obtain 230 mg of the title compound.

NMR (CD$_3$OD) δ: 8.20–8.16 (2H, m), 7.32 (1H, d), 3.80–3.78 (4H, m), 2.61–2.58 (4H, m), 2.37 (3H, s)

EXAMPLE 24

1-Allyl-1-methyl-4-(6-nitrobenzoxazol-2-yl) piperazinium iodide

Under cooling with ice, 50 mg of 2-(4-methyl-1-piperazinyl)-6-nitrobenzoxazole dissolved in 5 ml of DMF was mixed with 0.021 ml of allyl iodide, and the reaction was carried out for 1 hour at the same temperature and then for 19 hours at room temperature. The reaction mixture was concentrated under a reduced pressure, and the resulting residue was purified by Sephadex LH-20 (Pharmacia) (chloroform:methanol=1:1) to obtain 67 mg of the title compound.

NMR (CD$_3$OD) δ: 8.24 (1H, d), 8.20, 8.18 (1H, dd), 7.40 (1H, d), 6.23–6.13 (1H, m), 5.87–5.79 (2H, m), 4.31–4.26 (4H, m), 4.15–4.08 (2H, m), 3.80–3.69 (4H, m), 3.29 (3H, s)

EXAMPLE 25

2-(4-Methyl-1-piperazinyl)naphtho[2,3-d]oxazole

A 500 mg portion of 3-amino-2-naphthol dissolved in 100 ml of ethanol was mixed with 193 mg of potassium hydroxide. After 10 minutes of reaction, the resulting solution was mixed with 50 ml of carbon disulfide and refluxed under heating for 10 hours. The reaction solution was concentrated under a reduced pressure, and the resulting residue was dissolved in 100 ml of ethyl acetate, washed with water, dehydrated with sodium sulfate and then concentrated under a reduced pressure. Thereafter, the resulting residue was purified by a silica gel column chromatography (n-hexane:ethyl acetate=2:1) to obtain 600 mg of 2-mercaptonaphtho[2,3-d]benzoxazole.

A 100 mg portion of 2-mercaptonaphtho[2,3-d]oxazole dissolved in 30 ml of anhydrous benzene was mixed with 130 mg of phosphorus pentachloride, and the mixture was refluxed under heating for 2 hours. To this was further added 90 mg of phosphorus pentachloride, followed by additional 2.5 hours of heating under reflux. Under cooling with ice, 995 mg of N-methylpiperazine was added to the resulting solution, and the reaction was carried out for 1 hour at the same temperature and then for 48 hours at room temperature. Precipitated materials in the reaction solution were removed by filtration, and the resulting filtrate was concentrated under a reduced pressure. The thus obtained residue was dissolved in 300 ml of ethyl acetate, washed three times with water, dehydrated with sodium sulfate and then concentrated under a reduced pressure. The resulting residue was purified by a silica gel column chromatography (chloroform:methanol=50:1) to obtain 18 mg of the title compound.

NMR (CD$_3$OD) δ: 7.85–7.82 (2H, m), 7.68 (1H, d), 7.61 (1H, s), 7.40–7.33 (2H, m), 3.76 (4H, t), 2.58 (4H, t), 2.36 (3H s)

EXAMPLE 26

1-Allyl-1-methyl-4-(naphtho[2,3-d]oxazol-2-yl)piperazinium iodide

Under cooling with ice, 18 mg of 2-(4-methyl-1-piperazinyl)naphtho[2,3-d]oxazole dissolved in 5 ml of DMF was mixed with 14 mg of allyl iodide, and the reaction was carried out for 1 hour at the same temperature and then for 1.5 hours at room temperature. The reaction mixture was concentrated under a reduced pressure, and 10 ml of ethyl acetate was added to the resulting residue. Thereafter, the precipitate thus formed was collected by filtration, dissolved in 5 ml of water and then lyophilized to obtain 28 mg of the title compound.

NMR (CD3OD) δ: 7.90–7.88 (2H, m), 7.79 (1H, s), 7.72 (1H, s), 7.43–7.39 (2H, m), 6.21–6.10 (1H, m), 5.83–5.79 (2H, m), 4.30–4.19 (4H, m), 4.13–4.06 (2H, m), 3.75–3.64 (4H, m), 3.26 (3H, s)

Next, pharmacological effects of the compounds of the present invention are described in the following test examples.

TEST EXAMPLE 1

5-HT$_3$ Receptor Binding Affinity

Using a membrane fraction prepared from rat N1E-115 cells in accordance with the procedure of Lummis et al. (European Journal of Pharmacology, 189, 223–227, 1990), effects of the inventive compounds to inhibit binding of [$^3$H]-GR65630 which was radioligand 5-HT$_3$ antagonist to 5-HT$_3$ receptor were examined, with the results shown in Table 1.

TABLE 1

| | 5-HT$_3$ receptor binding affinity |
|---|---|
| Compound | Binding inhibitory ratio of [$^3$H]-GR65630 at $10^{-7}$ M |
| Example 1 | 89.4% |
| Example 2 | 45.5% |
| Example 3 | 52.8% |
| Example 4 | 48.0% |
| Example 5 | 78.0% |
| Example 13 | 97.3% |
| Example 14 | 44.4% |
| Example 16 | 46.0% |
| Example 19 | 54.3% |
| Example 22 | 51.6% |

TEST EXAMPLE 2

5-HT$_3$ Receptor Antagonism

In accordance with the procedure of Saxena et al. (Arch. Int. Pharmacodyn., 277, 235–252, 1985), each compound was dissolved in distilled water for injection to give different concentration and was administered intraperitoneally to mice which had been anesthetized with pentobarbital (3 animals per group), and ratio of inhibition of bradycardia induced by 5-HT administration (0.25 mg/kg, i.v.) was examined 30 minutes thereafter. The results are shown in Table 2.

TABLE 2

| | 5-HT$_3$ receptor antagonism | |
|---|---|---|
| Compound | Dose (mg/kg) | Inhibitory ratio |
| Example 1 | 3 | 76% |
| Example 3 | 0.3 | 82% |
| Example 5 | 0.3 | 61% |

TEST EXAMPLE 3

Antiemetic Effect in Cisplatin-Treated Dogs

Each of test dogs (2 animals per group) after 16 hours of fasting was fed with 200 g of a solid food, and cisplatin was administered to the animal 30 minutes thereafter by intravenous injection with a dose of 3 mg/kg. The test compound was dissolved in distilled water for injection and was administered by intravenous injection 30 minutes before and 2 hours after the cisplatin administration, and frequency and duration of emesis were observed over 6 hours. The results are shown in Table 3.

TABLE 3

| | Antiemetic effect in cisplatin-treated dogs | | |
|---|---|---|---|
| Compound | Dose (mg/kg) | Frequency of emesis (times) | Duration of emesis (hr) |
| Control | — | 13.5 | 2.63 |
| Example 3 | 0.1 × 2 | 0 | — |

While the invention has been described in detail and with reference to specific examples thereof, it will be apparent to one skilled in the art that various changes and modifications can be made therein without departing from the spirit and scope thereof.

What is claimed is:

1. A compound represented by the formula (1)

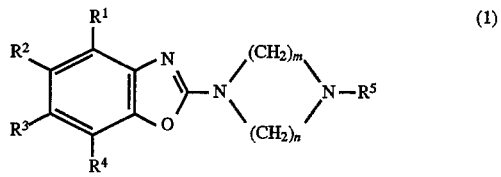

wherein $R^1$, $R^2$, $R^3$, $R^4$ may be the same or different and each represents a hydrogen atom, a substituted or unsubstituted lower alkyl group, a substituted or unsubstituted lower alkenyl group, a halogen atom, a hydroxyl group, an amino group, a lower alkoxyl group, a carboxyl group, a carbamoyl group or a nitro group, in which any two groups of $R^1$ to $R^4$ may be linked to each other to form a six-membered ring structure comprising carbon atoms alone, which may be substituted; $R^5$ represents a substituted or unsubstituted lower alkyl group, a substituted or unsubstituted lower alkenyl group, a substituted or unsubstituted aralkyl group containing 7 to 10 carbon atoms or an alkoxycarbonyl group, with the proviso that $R_5$ is a substituted alkyl group and is not an alkyl group substituted with an amino or dialkylamino group when $R_1$, $R_2$, $R_3$ and $R_4$ represent hydrogen atoms simultaneously; and m is an integer of 2 or 3 and n is an integer of 2; wherein each substituent is selected from the group consisting of a halogen atom, a hydroxyl group, a cyano group, an alkylcarbonyl group, an alkoxy group, a carboxyl group, an alkoxycarbonyl group, a carbamoyl group, an amino group and a nitro group; and said halogen atom is selected from the group consisting of fluorine, chlorine, bromine, and iodine.

2. A compound represented by the formula (2)

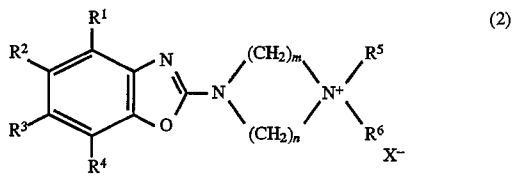

wherein $R^1$, $R^2$, $R^3$ and $R^4$ may be the same or different and each represents a hydrogen atom, a substituted or unsubstituted lower alkyl group, a substituted or unsubstituted lower alkenyl group, a halogen atom, a hydroxyl group, an amino group, a lower alkoxyl group, a carboxyl group, a carbamoyl group or a nitro group, in which any two groups of $R^1$ to $R^4$ may be linked to each other to form a six-membered ring structure comprising carbon atoms alone, which may be substituted; $R^5$ and $R^6$ may be the same or different and each represents a substituted or unsubstituted lower alkyl group, a substituted or unsubstituted lower alkenyl group, a substituted or unsubstituted aralkyl group containing 7 to 10 carbon atoms or an alkoxycarbonyl group, in which $R^5$ and $R^6$ may be linked to each other to form a five-membered ring structure comprising carbon atoms, which may be substituted, with the proviso that $R_5$ is a substituted alkyl group and is not an alkyl group substituted with an amino or dialkylamino group when $R_1$, $R_2$, $R_3$ and $R_4$ represent hydrogen atoms simultaneously; $X^-$ represents a pharmaceutically acceptable anion; and m is an integer of 2 or 3 and n is an integer of 2; wherein each substituent is selected from the group consisting of a halogen atom, a hydroxyl group, a cyano group, an alkylcarbonyl group, an alkoxy group, a carboxyl group, an alkoxycarbonyl group, a carbamoyl group, an amino group and a nitro group; and said halogen atom is selected from the group consisting of fluorine, chlorine, bromine, and iodine.

3. The compound according to claim 1, wherein said lower alkyl group contains 1 to 6 carbon atoms, said lower alkoxyl group contains 1 to 6 carbon atoms, said lower alkenyl group contains 2 to 6 carbon atoms and said aralkyl group contains 7 to 10 carbon atoms.

4. The compound according to claim 1, wherein said six-membered ring is selected from the group consisting of benzene and cyclohexane.

5. The compound according to claim 2, wherein said lower alkyl group contains 1 to 6 carbon atoms, said lower alkoxyl group contains 1 to 6 carbon atoms, said lower alkenyl, group contains 2 to 6 carbon atoms and said aralkyl group contains 7 to 10 carbon atoms.

6. The compound according to claim 2, wherein said six-membered ring formed by two groups of $R^1$ to $R^4$ is selected from the group consisting of benzene and cyclohexane.

7. The compound according to claim 2, wherein said pharmaceutically acceptable anion is selected from the group consisting of halogen ion, sulfate anion, phosphate anion, acetate anion and formate anion.

8. A serotonin 5-$HT_3$ receptor antagonist which comprises a therapeutically effective amount of the compound of claim 1 or 2 as an active ingredient and a pharmaceutically acceptable carrier.

9. A method of treating nausea and emesis which comprises administering to a patient a therapeutically effective amount of the compound of claim 1 or 2 and a pharmaceutically acceptable carrier.

* * * * *